(12) United States Patent
Ryan et al.

(10) Patent No.: US 6,794,152 B2
(45) Date of Patent: Sep. 21, 2004

(54) FLOW CYTOMETRY REAGENT AND SYSTEM

(75) Inventors: Wayne L. Ryan, Omaha, NE (US); Paula B. Turpen, Omaha, NE (US)

(73) Assignee: Streck Laboratories Inc., La Vista, NE (US)

( * ) Notice: Subject to any disclaimer, the term of this patent is extended or adjusted under 35 U.S.C. 154(b) by 0 days.

(21) Appl. No.: 09/747,619

(22) Filed: Dec. 22, 2000

(65) Prior Publication Data

US 2002/0119503 A1 Aug. 29, 2002

(51) Int. Cl.[7] ................................................. G01N 33/53
(52) U.S. Cl. .................... 435/7.24; 435/40.5; 435/69.6; 424/1.21; 436/15; 436/17; 436/18; 436/63; 436/66; 436/71
(58) Field of Search ............................. 436/15, 17, 18, 436/63, 66, 71; 435/40.5, 69.6; 424/1.21

(56) References Cited

U.S. PATENT DOCUMENTS

| | | |
|---|---|---|
| 4,654,312 A | 3/1987 | Chang et al. |
| 4,902,613 A | 2/1990 | Chang et al. |
| 5,188,935 A | 2/1993 | Leif et al. |
| 5,196,182 A | 3/1993 | Ryan |
| 5,250,438 A | 10/1993 | Ryan |
| 5,260,048 A | 11/1993 | Ryan |
| 5,270,208 A * | 12/1993 | Ryan ........................... 436/10 |
| 5,459,073 A | 10/1995 | Ryan |
| 5,460,797 A | 10/1995 | Ryan |
| 5,529,933 A * | 6/1996 | Young et al. .................. 436/10 |
| 5,731,206 A | 3/1998 | Ledis et al. |
| 5,776,709 A | 7/1998 | Jackson et al. |
| 5,786,224 A | 7/1998 | Li et al. |
| 5,811,099 A | 9/1998 | Ryan |
| 5,849,517 A | 12/1998 | Ryan |
| 5,879,900 A | 3/1999 | Kim et al. |
| 5,939,326 A | 8/1999 | Chupp et al. |
| 6,110,730 A | 8/2000 | Sams et al. |

OTHER PUBLICATIONS

Brown, Michael and Wittwer, Carl, "Flow Cytometry: Principles and Clinical Applications In Hematology," Clinical Chemistry, vol. 46 ( No. 8), p. 1221–1229, (2000).

U.S. 6337189 "Fixative System, Method and Composition for Biological Testing".

* cited by examiner

Primary Examiner—Bao-Thuy L. Nguyen
(74) Attorney, Agent, or Firm—Howrey Simon Arnold & White, LLP

(57) ABSTRACT

An improved reagent system for preparation of cells for flow cytometry having a physiologically compatible salt solution composition including a lysing agent, an agent for minimizing white blood cell lysis, and optionally a preservative.

11 Claims, 2 Drawing Sheets

FLOW CYTOMETRY REAGENT AND SYSTEM

FIELD OF THE INVENTION

The present invention generally relates to compositions useful for selectively lysing one or more components of blood while also achieving the stabilization of other components and, more particularly, for lysing erythrocytes while affording the stabilization necessary to preserve antigenic sites on the surface of leukocytes.

BACKGROUND OF THE INVENTION

The ability to differentiate and phenotype blood cells is useful for evaluating disease states and other health conditions in living beings. One popular technique for cell differentiation and lymphocyte immunophenotyping is flow cytometry. With flow cytometry, cells from an appropriately prepared blood sample, are passed one at a time through a flow cell, which is adapted for sensing or detecting impedance changes, light scatter or some other characteristic of the cell. Some flow cytometry instruments are equipped with detectors for measuring emissions from fluorescent tags that may be associated with the cells, while other detectors measure scatter intensity or pulse duration. Data about cells that pass through the flow cell can be plotted on a cytogram according to the measured property.

During the flow cytometry process, it is important that interference from the presence of erythrocytes (red blood cells) in the blood sample be avoided. Accordingly, during sample preparation, which may be done by manual, semi-automated or automated techniques), it is popular to employ a lytic reagent for lysing red blood cells and thereby isolating the leukocyte (white blood cell) populations. Leukocytes are known to include a myeloid fraction of monocytes and granulocytes (neutrophils, basophils and eosinophils) and a lymphoid fraction (namely NK, B and T cell lymphocytes). Each of the lymphocyte populations can be distinguished based upon the distinctive cell surface antigens or markers. Moreover, within each category of lymphocytes, there are sub-categories, such as "helper" T cells or "suppressor" T cells, the latter of which also includes several subsets, distinguishable by their respective surface markers. With flow cytometry of properly prepared cells, using polyclonal or monoclonal antibodies, it is possible to assay lymphocytes to analyze cells in the various subcategories.

For instance, to prepare a sample for fluorescent flow cytometry, according to one conventional practice, a volume of fresh sample blood is provided, and a suitable amount of a desired fluorochrome labeled antibody is added. The sample and antibody mixture is incubated to allow antibody/antigen bindings to take place. After incubation, a lytic reagent (some of which are regarded as potentially toxic, i.e., those containing formaldehyde) is added to lyse erythrocytes in the sample. The debris from the lysing of the erythrocytes is optionally removed, by washing, leaving a sample of leukocytes with antibodies bound to cells with complementary surface antigens. The sample is fixed and run through a fluorescent detecting flow cytometry instrument.

Among the items of potential interest to the present invention are Brown et al, "Flow Cytometry: Principles and Clinical Applications in Hematology", Clinical Chemistry 46:8(B), 1221–1229 (2000); U.S. Pat. Nos. 4,654,312; 4,902,613; 5,030,554; 5,188,935; 5,196,182; 5,250,438; 5,260,048; 5,459,073; 5,460,797; 5,731,206; 5,776,709; 5,811,099; 5,849,517, 5,939,326; 6,110,730; and commonly owned, co-pending U.S. patent application Ser. No. 09/500, 248 ("Fixative System, Method and Composition for Biological Testing"), the teachings of each of which are hereby expressly incorporated by reference for all purposes.

Accordingly, in view of the above, there is a need in the art for an improved lytic reagent that lyses red blood cells systematically and reproducibly preserves the surface antigen characteristics of leukocytes; that enables fixing of the leukocytes during the erythrocyte lysing step; that is non-toxic; and that can be used to prepare samples for analysis beyond one day.

SUMMARY OF THE INVENTION

As will be appreciated by one skilled in the art, the above needs are met individually or in combination, and other advantages are possible, by the employment of one or more novel compositions, each of which include effective amounts of a lytic agent, an agent for minimizing lysing of white blood cells (e.g., lipoprotein) and optionally a preservative. The composition of the present invention is particularly suited for use as a lytic reagent system for flow cytometry, but may also find suitable application in other analytical systems, such as hematology analyzers and microscopy.

DETAILED DESCRIPTION OF THE INVENTION

Figure 1:
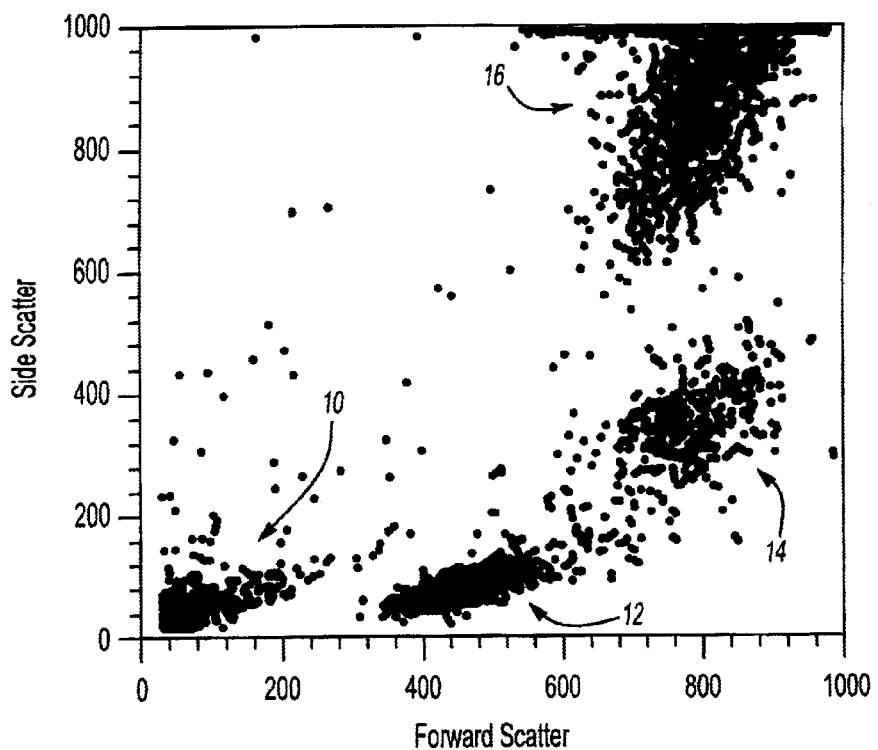
FIGS. 1–4 are cytograms for illustrating the advantages of the compositons of the present invention.

Parts and percentages herein are expressed by weight, unless otherwise noted. The term "lysis" (and its conjugates) as used herein shall mean to render cells no longer detectable by physical techniques. In the context of erythrocyte lysis, "lysis" shall refer to the rendering of erythrocyte residue (as represented, for instance, by reference numeral 10 in the Figures) so that any signals they might generate are minimized to avoid detectably interfering with those produced by the leukocytes.

A preferred composition in accordance with the present invention includes:

a) a lytic agent for lysing red blood cells;

b) an agent for minimizing lysing of white blood cells; and c) optionally a preservative for preserving white blood cells.

The active ingredients preferably are dissolved or suspended in a suitable physiological salt medium, such as a suitable saline, water or alcohol solution. A particularly preferred medium includes a metal salt (e.g., about 0.1 to about 2, more preferably about 0.5 to about 1.5, and still more preferably, about 0.9 percent by weight of the overall composition of metal halide salt) in distilled water.

The lytic agent of the present invention may be any suitable lytic agent. Preferably, however, the lytic agent is saponin, and it is present in an amount of about 0.1 to about 2 percent by weight of the overall composition, more preferably about 0.3 to about 1.5 percent, and still more preferably about 0.5 to about 1 percent. Examples of other suitable lytic agents include ammonium halides, such as dodecyltrimethyl ammonium chloride.

Though other constituents are possible, the agent for minimizing lysing of white blood cells preferably includes a lipoprotein. The lipoproteins suitable for use in the present invention can be either high or low density lipoproteins, both of which are available from a number of commercial sources. Lipoproteins from humans or the serum of various animals, (e.g. horse and bovine) and egg yolk lipoprotein may be used. It is also possible to use compositions containing lipoproteins as the lipoprotein source. Examples of such lipoprotein sources are animal (include man) blood serums and plasmas. Where such lipoprotein-containing compositions are employed, the amount of composition employed in the reference controls of the invention will depend upon the concentration of the lipoprotein. Preferred blood plasma or serum concentrates are those concentrated two to three fold so as to contain about 14 to 17% by weight of protein.

In a particularly preferred embodiment, the lipoprotein is a high density lipoprotein, such as that commercial available under the tradename SUPERTRATE® or MODUCYTE® from Bayer, or the like. In general such lipoprotein source compositions include a high density lipoprotein dispersed in a medium including about 25 mg/dl lipoprotein cholesterol/100 ml of product. Accordingly, about 0.01 to about 5 percent by weight of the overall composition is lipoprotein; more preferably about 0.1 to about 1 percent by weight; and still more preferably about 0.2 to about 0.5 percent by weight.

The composition of the present invention includes, in one preferred embodiment, a preservative (also regarded as a fixative) dispersed in a liquid medium. More preferably, the preservative is a chemical agent known widely in the art as a non-coagulating preservative or fixative. Thus, the preferred preservative when contacted with a biological specimen generally will exhibit only insubstantial denaturation (if any) of plasma protein substances in the biological material. It should be realized that in some instances a coagulating preservative may be employed in combination with or a non-coagulating preservative in accordance with certain aspects of the present invention, provided the resulting properties of the overall composition are not materially affected for purposes of handling or later pathological testing. In some instances, a coagulating preservative absent appreciable amounts of non-coagulating preservative may be employed advantageously.

Though other preservatives may be employed (e.g., aldehydes such as paraformaldehyde), the preservative of the compositions of the present invention preferably includes at least one non-crosslinking agent. One preferred class of preservatives includes a heterocyclic substituted urea in a buffered physiological salt solution. In another embodiment, the preservative is selected from the group consisting of diazolidinyl urea (DU), imidazolidinyl urea (IDU), polymethoxy bicyclic oxazolidine (e.g., NUOSEPT® 145 from Creanova Inc.) and mixtures thereof. Most preferably, the preservative is DU. The amount of preservative employed ranges up to about 5 percent by weight of the overall composition, more preferably about 0.5 to about 4 percent, and still more preferably about 2 to about 3 percent.

One popular technique for flow cytometry analysis, which may be employed in accordance with one aspect of the present invention involves the use of fluorescence techniques for cell analysis, in which cells are analyzed for the response of cell nucleic acid content, surface antigens or both to fluorescently tagged monoclonal or polyclonal antibodies or markers. The primary and secondary antibodies may be polyclonal, but are preferably monoclonal antibodies. Without limitation, illustrative examples of primary antibodies include, but are not limited to, a first fluorochrome label conjugated with the primary antibody.

If employed, one or more secondary antibody (polyclonal or monoclonal) may also be employed.

In general this labeling step involves staining a cell with an appropriate dye, or attaching a detectable fluorochrome label to the cell's surface, e.g., a fluorescently tagged antibody, the presence of which when detected would indicate the occurrence of a specific antigen-antibody reaction. Without limitation, examples of popular fluorochromes include fluorescein isothiocyanate, phycoerythrin (e.g., B- or R-type), propidium iodide, Texas Red, allophycocyanin or peridinin chlorophyl protein. Any of these fluorochromes, as well as others known in the art (including fluorochomes for two color, three color or four color approaches), can be used to label the primary and secondary antibodies of the invention using conjugation methods well known in the art.

The resulting pH of the composition (in its liquid state) of the present invention ranges from about −6 to about 9.5 and more preferably about 7 to about 8.5, and still more preferably about 8. The resulting composition may be contacted with cell samples and the samples preserved for as much as two, four or seven days or longer prior to analysis of the samples by flow cytometry. The resulting composition is also capable of stabilities for periods of 6 months or longer.

In a highly preferred embodiment, the resulting composition is:

|  | Range |
| --- | --- |
| Diazolidinyl urea | 1.0–6.0 gm/dl |
| Saponin | 10.0–300.0 mg/dl |
| Lipoprotein | 5.0–100.0 mg/dl of cholesterol |

Compositions in accordance with the present invention may also include other ingredients as desired and depending upon the intended application, such as (without limitation) mordants, buffers, surfactants, penetration increasers, osmotically active substances, nuclear detail improvers, and nuclear size increasers, such as addressed in U.S. Pat. No. 5,196,182, hereby expressly incorporated by reference. Examples of suitable mordants are salt of a metal having an oxidation state of two or more, e.g., zinc, strontium, calcium, barium, and chromium salts. The preferred salt is zinc sulfate. Suitable buffers include alkali metal phosphate salts, such as sodium phosphate and potassium phosphate. Osmotically active substances that may be included in the formulation of the invention are alkali metal salts, such as sodium chloride. In addition, sugars, such as the polysaccharides, sucrose, glucose, and the like, may be employed. Nuclear detail improvers and nuclear size increasers include acetic acid and lithium salts such as lithium chloride. Zinc salts, such as zinc sulfate, not only improve nuclear definition, but also improve staining. Illustrative of substances which increase the rate of penetration of the fixing agent are dimethylsulfoxide and ethanol.

The compositions of the present invention may be supplied as part of a kit, whose other components might include blood controls, other chemical reagents for a cytometry lab, a hematology instrument, a flow cytometer, sample preparation instruments, data management units or the like. It is also contemplated that any such instrument might be offered for sale as part of an agreement calling for a periodic replenishment of supply of the compositions of the present invention. The compositions may also be offered for sale in combination with one or more additional items such as those selected from glass slides, petri dishes, vials, flasks, beakers, storage and transport containers, handling instruments, protective clothing, preparatory chemicals, reagents, controls, readout devices, barcode scanners, data management kits, data forms, software, loaders, loader racks, labelers, coverslips or mixtures thereof. In another preferred embodiment, a composition of the present invention is provided in a kit including an immunostain, dye, a fluorochrome (or other tag), or the like, either with or without an associated monoclonal antibody. Kits or their respective components, including the composition of the present invention, may be offered for sale through a sales distributor, directly by the manufacturer, through a retail outlet, through a wholesale outlet, by mail order, over the internet, or otherwise. The compositions are preferably provided in a 5× concentrate, (though other concentrates may be used) in suitable bottles (e.g., 200 ml bottles) that can be packaged individually or in groups of two, three, four or more bottles.

The compositions of the present invention are useful for performing hematology analysis of samples in manual and automated instruments, with flow cytometers with hematology blood analyzers, with microscopy using optical microscopy, electron microscopy or the like. Samples prepared for analysis with the compositions of the present invention may be prepared using manual, semiautomated or automated techniques.

In one aspect of the present invention, a composition of the present invention is used for research, such as cancer research, AIDS research or otherwise. In another embodiment it is used for clinical diagnosis of patients. The composition may be used for analyzing blood of humans, other mammals, birds, reptiles, or other animals, in either a hospital, veterinary or other clinical or institutional setting.

In one embodiment, a composition in accordance with the present invention is contacted with a sample of blood infected by HIV. When the sample is processed, the DU or formaldehyde present in the sample stabilizes the white cells and inactivates HIV.

The compositions of the present invention may be used alone or in combination with other commercially available lytic reagents, including for example, IMMUNOPREP™ (Beckman Coulter), LYSE and FIX (Beckman Coulter), Q-Prep (Beckman Coulter) OPTILYSE (Beckman Coulter), FACS Lyse (Becton Dickinson), ERYTHROLYSE (Serotec), FLOWLYSE (Mallinckrodt), WHOLE BLOOD LYSE KIT (Caltag), UTI-LYSE (Dako), Q-LYSE (BioErgonomics, Inc.), ammonium chloride or the like. Moreover, active ingredients of the above may be substituted for or used in combination with the ingredients of the present compositions.

To prepare a sample for fluorescent flow cytometry, according to one method of the present invention, a predetermined volume of fresh sample blood is provided, and a suitable amount of the desired fluorochrome labeled monoclonal antibody is added. The sample and antibody mixture is then incubated for a predetermined time (e.g., about 10 to about 30 minutes) at a predetermined temperature to allow antibody and antigen bindings to take place. Sample may then be washed and resuspended as desired. After incubation, the composition of the present invention is contacted with the sample to lyse erythrocytes in the sample. Such contacting step occurs for a period of time sufficient so that any erythrocytes that remain in the sample will not materially distort measurements, but not so long that leukocytes will be damaged. The debris from the lysing of the erythrocytes is optionally removed, by washing, leaving a sample of leukocytes with antibodies bound to cells with complementary surface antigens. The sample is then run through a fluorescence detecting flow cytometry instrument. In another embdiment, the composition of the present invention is contacted with the cells prior to labeling and incubation.

In accordance with the above, it will be appreciated that among the advantages of the compositions of the present invention are that the compositions of the present invention can be formulated as nontoxic compositions. Reproducible cytometric results are obtainable after delays from sample collection or preparation to testing. The compositions can be used in wash and no wash systems. Samples can be lysed before or after staining with markers, or otherwise tagging, with no adverse effect upon fluorescence or disruption of cell surface markers. The compositions can be used as a fixation-permeation agent. As well as providing good fluorescence cytometric analysis, the compositions exhibit good retention of light scatter characteristics, good signal to noise ratio, and the ability to gate (or otherwise isolate a sample portion by electronic logic with a physical measurement) well for purposes of forward light scatter and side light scatter instruments. The compositions are thus suitable for use in a variety of commercially available instruments, such as (without limitation) available from Becton Dickinson under its FACS™ designation, such as (without limitation) FACSCalibur, FACSVantage, or instruments employing like technology; from Beckman Coulter under the designation EPICS® (as well as associated sample preparation stations such as its Q-PREP line; from Abbott Laboratories under the CELL-DYN™ designation (e.g., Cell-Dyn 4000).

The present invention is further illustrated by reference to the following Examples, which are illustrative only and not intended as limiting.

EXAMPLES

Example 1

Figure 2:
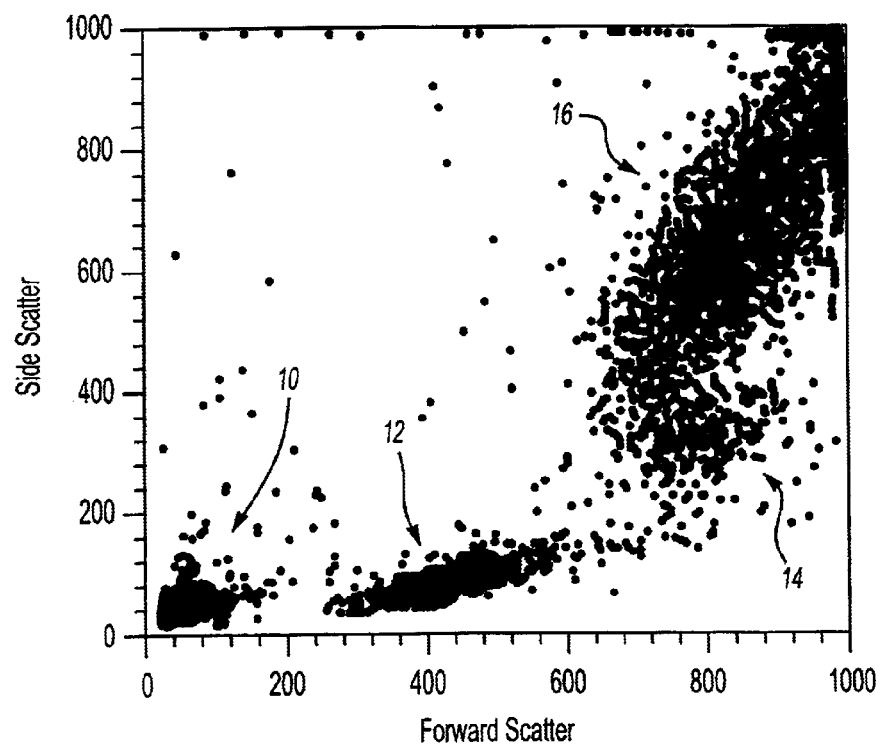

Human blood samples are prepared for flow cytometry. A first sample (Sample A) is treated with the composition prepared by adding to unheated distilled water in the following order: 9 g/l NaCl; 30 g/l DU; 0.25 g/l high density lipoprotein cholesterol; and 0.7 g/l saponin. A second sample (Sample B) is treated with a prior art composition including conventional amounts of diethylene glycol, formaldehyde and distilled water. The samples are analyzed by a flow cytometer on the day they are drawn. Sample A yields a cytogram such as depicted in FIG. 1, having four identifiable clusters corresponding respectively to cell populations of debris from lysed red blood cells 10, lymphocytes 12, monocytes 14 and granulocytes 16. Sample B yields a cytogram such as depicted in FIG. 2, where like components are represented by like reference numerals. The cytogram of FIG. 1 exhibits better resolution, brighter intensity and improved light scatter.

Example 2

Figure 3:
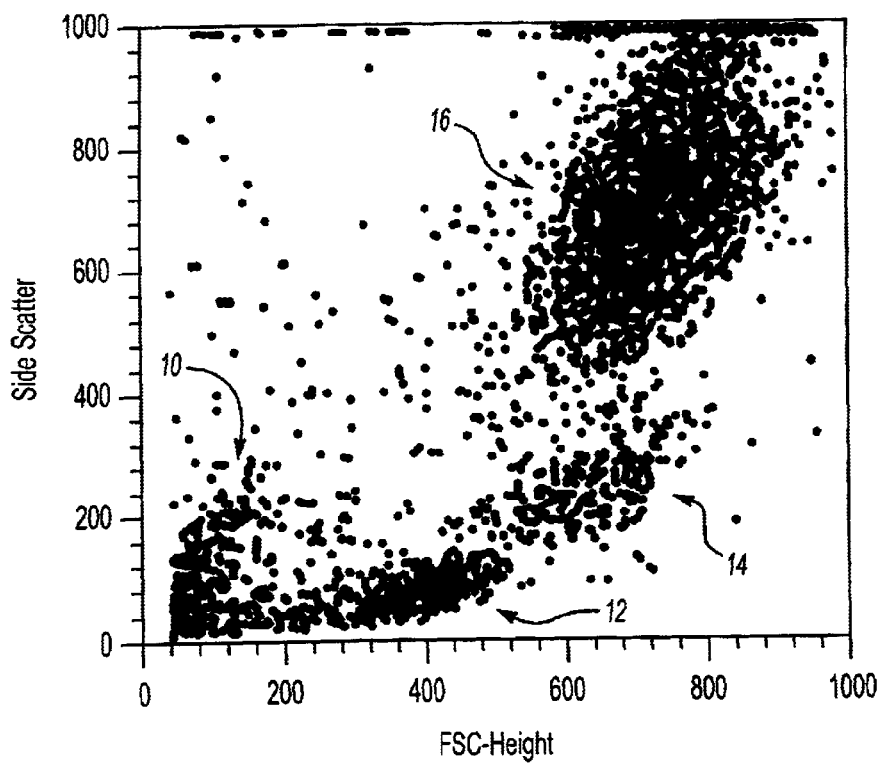
Figure 4:
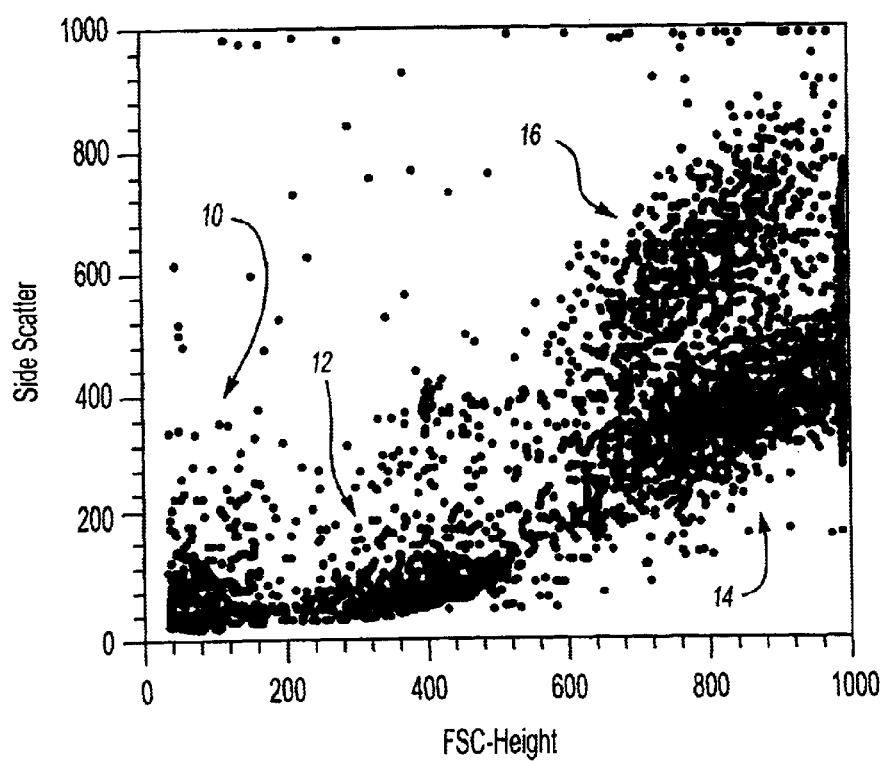

The samples of Example 1 are analyzed by a flow cytometer 48 hours after they are drawn. Sample A yields a cytogram such as depicted in FIG. 3 and Sample B yields a cytogram such as depicted in FIG. 4 (again, where like components are represented by like reference numerals). A comparison of FIGS. 1 and 3 shows similar results are obtained and confirm sample stability. A comparison of FIGS. 2 and 4 shows a significant visible deviation.

Example 3

Sample A is employed in a wash preparatory method and a no wash preparatory method, and similar results are obtained as in Example 1, the same day as the sample is drawn, as well as 48 hours.

The illustrative embodiments set forth in the above constitute examples of the principles of the present invention. Numerous alternatives will readily occur to the person skilled in the art, without departing from the scope of the present invention as set forth in the following claims.

What is claimed is:

1. A reagent composition for flow cytometric analysis of a sample of fresh human blood, comprising:
   a. a lipoprotein in contact with leukocytes of said sample of fresh human blood for minimizing lysis of said leukocytes;
   b. an agent for lysing erythrocytes from said sample of fresh blood for permitting flow cytometric analysis of said leukocytes; and
   c. a preservative selected from the group consisting of diazolidinyl urea (DU), imidazolidinyl urea (IDU), an oxazolidine and mixtures thereof.

2. The composition of claim 1 further comprising an effective amount of a physiologically compatible salt.

3. The composition of claim 1 wherein said lipoprotein is a high density lipoprotein.

4. The composition of claim 1 wherein said agent for lysing is saponin.

5. The composition of claim 1 further comprising a sample preparation instrument for preparing a whole blood sample for flow cytometric analysis.

6. The composition of claim 1 further comprising an antibody for binding with a surface antigen of at least one of said leukocytes.

7. The composition of claim 6 further comprising a fluorochrome associated with said antibody.

8. The composition of claim 6 wherein said antibody is a monoclonal antibody.

9. A reagent composition for cytometric analysis of a sample of fresh human blood, comprising:
   a. a high density lipoprotein in contact with leukocytes of said sample of fresh human blood for minimizing lysis of said leukocytes;
   b. about 0.1 to about 2 percent by weight of an agent for lysing erythrocytes from a sample of fresh blood for permitting cytometric analysis of said leukocytes; and
   c. upto about 5 percent by weight of a preservative selected from the group consisting of diazolidinyl urea (DU), imidazolidinyl urea (IDU), an oxazolidine and mixtures thereof.

10. A reagent composition for cytometric analysis of a sample of fresh human blood, comprising:
   a. about 0.01 to about 5 percent by weight of a high density lipoprotein in contact with leukocytes of said sample of fresh human blood for minimizing lysis of said leukocytes;
   b. about 0.1 to about 2 percent by weight of an agent for lysing erythrocytes from a sample of fresh blood for permitting cytometric analysis of said leukocytes; and
   c. upto about 5 percent by weight of diazolidinyl urea (DU).

11. A reagent composition for preparing leukocytes for cytometric analysis, comprising:
   a. about 0.01 to about 5 percent by weight of a high density lipoprotein;
   b. about 0.1 to about 2 percent by weight of an agent for lysing erythrocytes from a sample of fresh blood for permitting cytometric analysis of said leukocytes;
   c. upto about 5 percent by weight of diazolidinyl urea (DU); and
   d. about 0.1 to about 2 percent by weight of a halide salt.

* * * * *

UNITED STATES PATENT AND TRADEMARK OFFICE
CERTIFICATE OF CORRECTION

| | | |
|---|---|---|
| PATENT NO. | : 6,794,152 B2 | Page 1 of 1 |
| APPLICATION NO. | : 09/747619 | |
| DATED | : September 21, 2004 | |
| INVENTOR(S) | : Wayne L. Ryan and Paula B. Turpen | |

It is certified that error appears in the above-identified patent and that said Letters Patent is hereby corrected as shown below:

Claim 9, column 8, line 9, delete "upto" and insert -- up to --.

Claim 10, column 8, line 22, delete "upto" and insert -- up to --.

Claim 11, column 8, line 31, delete "upto" and insert -- up to --.

Signed and Sealed this

Tenth Day of July, 2007

JON W. DUDAS
*Director of the United States Patent and Trademark Office*